United States Patent [19]
Riedel et al.

[11] Patent Number: 6,040,469
[45] Date of Patent: Mar. 21, 2000

[54] METALLOCENE COMPOUND

[75] Inventors: Michael Riedel, Essen; Thomas Weller, Mainz; Alexandra Jacobs, Frankfurt; Wolfgang Anton Herrmann, Freising; Markus Morawietz, Hanau, all of Germany

[73] Assignee: Targor GmbH, Germany

[21] Appl. No.: 08/764,526

[22] Filed: Dec. 12, 1996

[30] Foreign Application Priority Data

Dec. 13, 1995 [DE] Germany .............. 195 46 501

[51] Int. Cl.⁷ .................................. C07F 17/00
[52] U.S. Cl. .............. 556/53; 502/103; 526/129; 526/160
[58] Field of Search ............... 556/53; 502/103; 526/129, 160

[56] References Cited

U.S. PATENT DOCUMENTS

| | | | |
|---|---|---|---|
| 5,529,966 | 6/1996 | Luciani et al. | 502/117 |
| 5,594,081 | 1/1997 | Uchino et al. | 526/127 |
| 5,700,749 | 12/1997 | Tsutsui et al. | 526/129 |

FOREIGN PATENT DOCUMENTS

| | | |
|---|---|---|
| 0 498 675 | 8/1992 | European Pat. Off. . |
| 498675 | 8/1992 | European Pat. Off. . |
| 95/32979 | 10/1995 | WIPO . |
| 95/27717 | 12/1995 | WIPO . |
| 95/32979 | 12/1995 | WIPO . |

*Primary Examiner*—David W. Wu
*Assistant Examiner*—Ling-Siu Choi
*Attorney, Agent, or Firm*—Connolly Bove Lodge & Hutz LLP

[57] ABSTRACT

The present invention relates to a metallocene compound of the formula I,

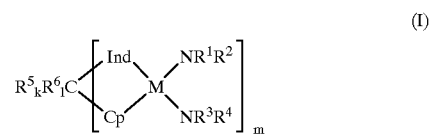

where Cp is an unsubstituted or substituted cyclopentadienyl group, Ind is unsubstituted or substituted indenyl, M is a tetravalent metal, $R^1$, $R^2$, $R^3$ and $R^4$ are, independently of one another, identical or different and are each a hydrogen atom or a $C_1$–$C_{20}$-hydrocarbon radical, $R^5$ and $R^6$ are, independently of one another, identical or different and are each a hydrogen atom or a $C_1$–$C_{20}$-hydrocarbon radical, m is 1 or 2 and k and l are 1 when m is 1 when m is 1 and k and l are zero when m is 2. The metallocene compound is suitable as a catalyst component for olefin polymerization.

19 Claims, No Drawings

METALLOCENE COMPOUND

The present invention relates to a metallocene compound and a process for preparing a polyolefin in the presence of this metallocene compound.

Metallocene compounds of the 4th transition group of the Periodic Table of the Elements are, in combination with methylaluminoxane (MAO), active catalysts for the polymerization of olefins. The literature discloses the preparation of polyolefins using soluble metallocene compounds in combination with aluminoxanes or other cocatalysts which, owing to their Lewis acidity, can convert the neutral metallocene into a cation and stabilize it (EP-A-129 368).

Metallocene and semisandwich complexes are of great interest, not only with regard to the polymerization or oligomerization of olefins. They can also be used as hydrogenation, epoxidation, isomerization and C—C coupling catalysts (Chem. Rev. 1992, 92, 965–994).

It is known from the literature that CpH can be reacted with zirconium or hafnium dimethyltetraamide, directly and without addition of a base, to give metallocenes of the types described in EP-A-595 390 and EP-A-283 164 (J. Chem. Soc. (A), 1968, 1940–1945). It is an object of the invention to provide a novel metallocene compound and an economical process for preparing polyolefins. This object is achieved by the metallocene compound of the present invention.

The present invention accordingly provides a metallocene compound of formula I

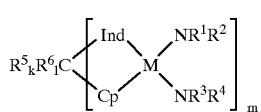

(I)

where Cp is an unsubstituted or substituted cyclopentadienyl group, Ind is unsubstituted or substituted indenyl, M is a tetravalent metal, $R^1$, $R^2$, $R^3$ and $R^4$ are, independently of one another, identical or different and are each a hydrogen atom or a $C_1$–$C_{20}$-hydrocarbon radical, $R^5$ and $R^6$ are, independently of one another, identical or different and are each a hydrogen atom or a $C_1$–$C_{20}$-hydrocarbon radical, m is 1 or 2 and k and l are 1 when m is 1 and k and l are zero when m is 2.

M is preferably titanium, zirconium, hafnium, vanadium, niobium, tantalum, scandium, yttrium or a rare earth metal, particularly preferably titanium, zirconium or hafnium.

Cp is an unsubstituted or substituted cyclopentadienyl group. Examples of substituted cyclopentadienyl groups are: tetramethylcyclopentadienyl, methylcyclopentadienyl, methyl-tert-butylcyclopentadienyl, tert-butylcyclopentadienyl, isopropylcyclopentadienyl, dimethylcyclopentadienyl, trimethylcyclopentadienyl, trimethylsilylcyclopentadienyl, trimethylethylcyclopentadienyl, phenylcyclopentadienyl, diphenylcyclopentadienyl, indenyl, 2-methylindenyl, 2-ethylindenyl, 3-methylindenyl, 3-tert-butylindenyl, 3-trimethylsilylindenyl, 2-methyl-4-phenylindenyl, 2-ethyl-4-phenylindenyl, 2-methyl-4-naphthyl-indenyl, 2-methyl-4-isopropylindenyl, 4,5-benzoindenyl, 2-methyl-4,5-benzoindenyl, 2-methyl-α-acenaphthindenyl, 2-methyl-4,6-diisopropylindenyl, fluorenyl, 4-methylfluorenyl or 2,7-di-tert-butylfluorenyl.

Ind is unsubstituted or substituted indenyl. Examples of substituted indenyl are: 2-methylindenyl, 2-ethylindenyl, 2-isopropylindenyl, 3-methylindenyl, 3-tert-butylindenyl, 3-trimethylsilylindenyl, 2-methyl-4-phenylindenyl, 2-ethyl-4-phenylidenyl, 2-methyl-4-naphthylindenyl, 2-methyl-4-isopropylindenyl, 4,5-benzoindenyl, 2-methyl-4,5-benzoindenyl, 2-methyl-α-acenaphthindenyl, 2-methyl-4,6-diisopropylindenyl. Ind is preferably unsubstituted indenyl.

The radicals $R^5$ and $R^6$ are, independently of one another, identical or different, preferably identical, and are each a hydrogen atom or a $C_1$–$C_{30}$-hydrocarbon radical such as $C_1$–$C_{20}$-alkyl or $C_6$–$C_{14}$-aryl. $R^5$ and $R^6$ are preferably methyl, ethyl, butyl or phenyl, in particular methyl.

$R^1$ and $R^3$ are, independently of one another, identical or different and are each a hydrogen atom or a $C_1$–$C_{20}$-hydrocarbon radical, preferably a $C_1$–$C_{20}$-hydrocarbon radical such as $C_1$–$C_{20}$-alkyl or $C_6$–$C_{14}$-alkyl, in particular methyl.

$R^2$ and $R^4$ are, independently of one another, identical or different and are preferably each a $C_1$–$C_{20}$-hydrocarbon radical such as $C_1$–$C_{20}$-alkyl or $C_6$–$C_{14}$-aryl, in particular methyl.

The radicals $R^1$, $R^2$, $R^3$ and $R^4$ are, independently of one another, identical or different. Preferably, the radicals $R^1$, $R^2$, $R^3$ and $R^4$ are identical and are each a $C_1$–$C_{20}$-hydrocarbon radical such as $C_1$–$C_{20}$-alkyl or $C_6$–$C_{14}$-aryl, in particular methyl. m is preferably 1.

Examples of metallocene compounds of the formula I are:
bis(dimethylamido)[$\eta^5$:$\eta^5$-2,2-(cyclopentadienyl)(indenyl)propylidene)]-zirconium
bis(dimethylamido)[$\eta^5$:$\eta^5$-2,2-(cyclopentadienyl)(indenyl)propylidene)]-hafnium
bis(dimethylamido)[$\eta^5$:$\eta^5$-2,2-(fluorenyl)(indenyl)propylidene)]zirconium
bis(dimethylamido)[$\eta^5$:$\eta^5$-2,2-(fluorenyl)(indenyl)propylidene)]hafnium
bis(dimethylamido)[$\eta^5$:$\eta^5$-2,2-(methylcyclopentadienyl)(indenyl)propylidene)]zirconium
bis(dimethylamido)[$\eta^5$:$\eta^5$-2,2-(fluorenyl)(2-methylindenyl)propylidene)]-zirconium
bis(dimethylamido)[$\eta^5$:$\eta^5$-2,2-(tetramethylcyclopentadienyl)(indenyl)propylidene)]zirconium
bis(dimethylamido)[$\eta^5$:$\eta^5$-2,2-(fluorenyl)(2-ethylindenyl)propylidene)]-zirconium
bis(dimethylamido)[$\eta^5$:$\eta^5$-2,2-(cyclopentadienyl)(2-methylindenyl)propylidene)]zirconium
bis(dimethylamido)[$\eta^5$:$\eta^5$-2,2-(cyclopentadienyl)(2-ethylindenyl)propylidene)]-zirconium
bis(dimethylamido)[$\eta^5$:$\eta^5$-2,2-(cyclopentadienyl)(3-trimethylsilylindenyl)propylidene)]zirconium
bis(dimethylamido)[$\eta^5$:$\eta^5$-2,2-(methylcyclopentadienyl)(2-methylindenyl)propylidene)]zirconium
bis(dimethylamido)[$\eta^5$:$\eta^5$-2,2-(methylcyclopentadienyl)(2-ethylindenyl)propylidene)]zirconium
bis(dimethylamido)[$\eta^5$:$\eta^5$-2,2-(methylcyclopentadienyl)(3-trimethylsilylindenyl)propylidene)]zirconium
bis(dimethylamido)[$\eta^5$:$\eta^5$-2,2-(2-methylindenyl)(3-trimethylsilylindenyl)(propylidene)]zirconium
bis(dimethylamido)[$\eta^5$:$\eta^5$-2,2-(indenyl)(3-trimethylsilylindenyl)(propylidene)]zirconium
bis(dimethylamido)[$\eta^5$:$\eta^5$-2,2-(2-methylindenyl)(indenyl)(propylidene)]zirconium
bis(dimethylamido)[$\eta^5$:$\eta^5$-2,2-bis(indenyl)propylidene)]-zirconium.

Further examples are the analogous bis(diethylamido)-, bis(methylethylamide)- and bis(pyrrolidinoamido) zirconium compounds.

The metallocenes of the invention are highly active catalyst components for olefin polymerization. Depending on the substitution pattern of the ligands, the metallocenes can be obtained as a mixture of isomers. The metallocenes are preferably used as pure isomers. The use of the racemate is sufficient in most cases.

It is also possible to use the pure enantiomer in the (+) or (−) form. The pure enantiomers enable an optically active polymer to be prepared. However, the configurational isomers of the metallocenes should be removed, since the polymerization-active center (the metal atom) in these compounds produces a polymer having different properties. For certain applications, for example soft moldings, this can be thoroughly desirable.

The metallocene compound of the formula I can be prepared by reacting a compound of the formula II, where Cp is an unsubstituted or substituted cyclopentadienyl group, Ind is unsubstituted or substituted indenyl, $R^5$ and $R^6$ are, independently of one another, identical or different and are each a hydrogen atom or a $C_1$–$C_{20}$-hydrocarbon radical, m is 1 or 2 and k and l are 1 when m is 1 and k and l are zero when m is 2, with a compound of the formula III, where M is a tetravalent metal and $R^1$, $R^2$, $R^3$ and $R^4$ are, independently of one another, identical or different and are each a hydrogen atom or a $C_1$–$C_{20}$-hydrocarbon radical.

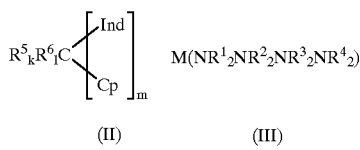

(II)   (III)

The reaction is preferably carried out in an aproptic solvent, e.g. toluene or hexane. The temperature can be between −78 and 140° C., preferably from 0° C. to 110° C. The compound of the formula II can be used in excess, preference is given to using 1 equivalent of the compound of the formula II and 1 equivalent of the metal tetramide of the formula III.

Processes for preparing compounds of the formula II are known (Chem. Ber. 1990, 123, 1649–1651). Processes for preparing compounds of the formula III are likewise known (J. Chem. Soc. 1960, 3857–3861).

The present invention also provides a process for preparing a polyolefin by polymerization of at least one olefin in the presence of a catalyst comprising at least one cocatalyst and at least one metallocene compound of the formula I.

For the purposes of the present invention, the term polymerization refers to both homopolymerization and copolymerization. In the process of the invention, preference is given to polymerizing one or more olefins of the formula $R^a$—CH=CH—$R^b$, where $R^a$ and $R^b$ are identical or different and are each a hydrogen atom or a hydrocarbon radical having from 1 to 20 carbon atoms, in particular from 1 to 10 carbon atoms, and $R^a$ and $R^b$ together with the atoms connecting them can form one or more rings. Examples of such olefins are 1-olefins having from 2 to 40, preferably from 2 to 10, carbon atoms, for example ethylene, propylene, 1-butene, 1-pentene, 1-hexene, 4-methyl-1-pentene or 1-octene, styrene, dienes such as 1,3-butadiene, isoprene or 1,4-hexadiene or cyclic olefins. In the process of the invention, preference is given to homopolymerizing ethylene or propylene or copolymerizing ethylene with one or more acyclic 1-olefins having from 3 to 20 carbon atoms, e.g. propylene, and/or one or more dienes having from 4 to 20 carbon atoms, e.g. 1,3-butadiene. Examples of such copolymers are ethylene-propylene copolymers and ethylene-propylene-1,4-hexadiene copolymers.

The polymerization is preferably carried out at a temperature from −60 to 250° C., particularly preferably from 50 to 200° C. The pressure is preferably from 0.5 to 2000 bar, particularly preferably from 5 to 64 bar.

The polymerization can be carried out in solution, in bulk, in suspension or in the gas phase, continuously or batchwise, in one or more stages. Preferred embodiments are gas-phase and solution polymerization.

The catalyst used in the process of the invention preferably comprises a metallocene compound of the formula I and a cocatalyst. It is also possible to use mixtures of two or more metallocene compounds, for example for preparing polyolefins having a broad or multimodal molecular weight distribution.

In principle, a suitable cocatalyst in the process of the invention is any compound which, owing to its Lewis acidity can convert the neutral metallocene into a cation and stabilize the latter ("labile coordination"). Furthermore, the cocatalyst or the anion formed therefrom should undergo no further reactions with the metallocene cation formed (EP 427 697). The cocatalyst used is preferably an aluminum compound and/or a boron compound.

The boron compound preferably has the formula $R^7_x NH_{4-x} BR^8_4$, $R^7_x PH_{4-x} BR^8_4$, $R^7_3 CBR^8_4$ or $BR^8_3$, where x is from 1 to 4, preferably 3, the radicals $R^7$ are identical or different, preferably identical, and are $C_1$–$C_{10}$-alkyl or $C_6$–$C_{18}$-aryl, or two radicals $R^7$ together with the atoms connecting them form a ring, and the radicals $R^8$ are identical or different, preferably identical, and are $C_6$–$C_{18}$-aryl which may be substituted by alkyl, haloalkyl or fluorine. In particular, $R^7$ is ethyl, propyl, butyl or phenyl and $R^8$ is phenyl, pentafluorophenyl, 3,5-bis(trifluoromethyl)phenyl, mesityl, xylyl or tolyl (EP-A-277 003, EP-A-277 004 and EP-A-426 638).

The cocatalyst used is preferably an aluminum compound such as aluminoxane and/or an aluminum alkyl.

The cocatalyst used is particularly preferably an aluminoxane, in particular of the formula IVa for the linear type and/or the formula IVb for the cyclic type,

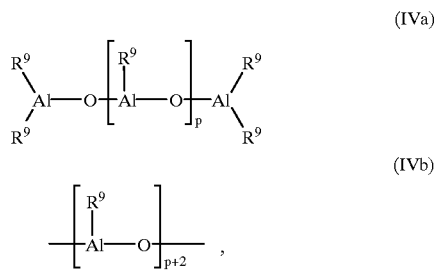

where, in the formulae IVa and IVb, the radicals $R^9$ are identical or different and are each hydrogen or a $C_1$–$C_{20}$-hydrocarbon group such as a $C_1$–$C_{18}$-alkyl group, a $C_6$–$C_{18}$-aryl group or benzyl and p is an integer from 2 to 50, preferably from 10 to 35.

The radicals $R^9$ are preferably identical and are hydrogen, methyl, isobutyl, phenyl or benzyl, particularly preferably methyl.

If the radicals $R^9$ are different, they are preferably methyl and hydrogen or alternatively methyl and isobutyl, with hydrogen or isobutyl preferably being present in a proportion of from 0.01 to 40% by number (of the radicals $R^9$).

The methods of preparing the aluminoxanes are known. The exact spatial structure of the aluminoxanes is not known (J. Am. Chem. Soc. (1993) 115, 4971). For example, it is conceivable that chains and rings are joined to form larger two-dimensional or three-dimensional structures.

Regardless of the method of preparation, all aluminoxane solutions have in common a varying content of unreacted aluminum starting compound which is present in free form or as adduct.

It is possible to preactivate the metallocene compound using a cocatalyst, in particular an aluminoxane, prior to use in the polymerization reaction. The significantly increases the polymerization activity. The preactivation of the metallocene compound is preferably carried out in solution. The metallocene compound is preferably dissolved in a solution of the aluminoxane in an inert hydrocarbon. Suitable inert hydrocarbons are aliphatic or aromatic hydrocarbons. Preference is given to using toluene.

The concentration of the aluminoxane in the solution is in the range from about 1% by weight to the saturation limit, preferably from 5 to 30% by weight, in each case based on the total amount of solution. The metallocene can be used in the same concentration, but it is preferably used in an amount of from $10^{-4}$ to 1 mol per mol of aluminoxane. The preactivation time is from 5 minutes to 60 hours, preferably from 5 to 60 minutes. The preactivation is carried out at a temperature of from −78 to 100° C., preferably from 0 to 80° C.

The metallocene compound is preferably employed in a concentration, based on the transition metal, of from $10^{-3}$ to $10^{-8}$ mol, preferably from $10^{-4}$ to $10^{-7}$ mol, of transition metal per $dm^3$ of solvent or per $dm^3$ of reactor volume. The aluminoxane is preferably used in a concentration of from $10^{-6}$ to $10^{-1}$ mol, preferably from $10^{-5}$ to $10^{-2}$ mol, per $dm^3$ of solvent or per $dm^3$ of reactor volume. The other cocatalysts mentioned are used in approximately equimolar amounts to the metallocene compound. However, high concentrations are also possible in principle.

The aluminoxane can be prepared in various ways by known methods. One of the methods is, for example, reacting an aluminum hydrocarbon compound and/or a hydridoaluminum hydrocarbon compound with water (gaseous, solid, liquid or bound —for example as water of crystallization) in an inert solvent (for example toluene). To prepare an aluminoxane having different radicals $R^{24}$, for example, two different trialkylaluminums corresponding to the desired composition are reacted with water.

To remove catalyst poisons present in the olefin, purification using an aluminum compound, preferably an aluminum alkyl such as trimethylaluminum or triethylaluminum, is advantageous. This purification can be carried out either in the polymerization system itself or the olefin is brought into contact with the aluminum compound and subsequently separated off again prior to addition to the polymerization system.

Hydrogen can be added in the process of the present invention to regulate the molecular weight add/or to increase the catalyst activity. This enables low molecular weight polyolefins such as waxes to be obtained.

In the process of the invention, the metallocene compound is preferably reacted with the cocatalyst outside the polymerization reactor in a separate step using a suitable solvent. The catalyst can be applied to a support during this step.

In the process of the invention, a prepolymerization can be carried out with the aid of the metallocene compound. The prepolymerization is preferably carried out using the (or one of the) olefin(s) used in the polymerization.

The catalyst used in the process of the invention can be supported. The application to the support enables, for example, the particle morphology of the polyolefin prepared to be controlled. Here, the metallocene compound can be reacted first with the support and subsequently with the cocatalyst. It is also possible for the cocatalyst to be supported first and subsequently reacted with the metallocene compound. It is also possible to apply the reaction product of metallocene compound and cocatalyst to a support. Suitable support materials are, for example, silica gels, aluminum oxides, solid aluminoxane or other inorganic support materials such as magnesium chloride. Another suitable support material is a polyolefin powder in finely divided form. The preparation of the supported cocatalyst can be carried out, for example, as described in EP-A-567 952.

The cocatalyst, e.g., aluminoxane, is preferably applied to a support such as silica gel, aluminum oxide, solid aluminoxane, another inorganic support material or a polyolefin powder in finely divided form and then reacted with the metallocene.

Inorganic supports which can be used are oxides which have been produced flame-pyrolytically by combustion of element halides in a hydrogen/oxygen flame or can be prepared as silica gels in particular particle size distributions and particle shapes.

The supported cocatalyst can be prepared, for example as described in EP-A-578 838, in the following manner in a stainless steel reactor of explosion-proof design having a 60 bar pumped circulation system, an inert gas supply, temperature regulation by jacket cooling and a second cooling circuit via a heat exchanger on the pumped circulation system. The pumped circulation system draws the contents of the reactor in via a connection in the reactor bottom by means of a pump and pushes it into a mixer and through a riser line via a heat exchanger back into the reactor. The mixer is configured such that in the inlet section there is a constricted tube cross-section in which the flow velocity is increased and in whose turbulence zone there is arranged, axially and counter to the flow direction, a thin feed line through which, pulsed, a defined amount of water under 40 bar of argon can be fed in. The reaction is monitored via a sampler on the pumped circuit. However, other reactors are also suitable in principle.

Further possible ways of preparing a supported cocatalyst are described in EP-A-578 838. In this method, the metallocene of the invention is applied to the supported cocatalyst by stirring the dissolved metallocene with the supported cocatalyst. The solvent is removed and replaced by a hydrocarbon in which both the cocatalyst and the metallocene are insoluble.

The reaction to form the supported catalyst system can be carried out at a temperature of from −20 to +120° C., preferably from 0 to 100° C., particularly preferably from 15 to 40° C. The metallocene is reacted with the supported cocatalyst by combining a suspension of from 1 to 40% by weight, preferably from 5 to 20% by weight, of the cocatalyst in an aliphatic, inert suspension medium such as n-decane, hexane, heptane or diesel oil with a solution of the metallocene in an inert solvent such as toluene, hexane, heptane or dichloromethane or with the finely ground solid of the metallocene. The other way around, it is also possible to react a solution of the metallocene with the solid of the cocatalyst.

The reaction is carried out by means of intensive mixing, for example by stirring at a molar $Al/M^1$ ratio of from 100/1 to 10000/1, preferably from 100/1 to 3000/1, for a reaction time of from 5 to 120 minutes, preferably from 10 to 60 minutes, particularly preferably from 10 to 30 minutes, under inert conditions.

During the reaction time for preparing the supported catalyst system, changes occur in the color of the reaction mixture, particularly when using the metallocenes of the invention having absorption maxima in the visible region, and the progress of the reaction can be followed by means of these color changes.

After the reaction time has elapsed, the supernatant solution is separated off, for example by filtration or decantation. The remaining solid is washed from 1 to 5 times with an inert suspension medium such as toluene, n-decane, hexane, diesel oil or dichloromethane to remove soluble constituents in the catalyst formed, in particular to remove unreacted and therefore soluble metallocene.

The supported catalyst system thus prepared can be resuspended as a vacuum-dried powder or while still moist with solvent and metered into the polymerization system as a suspension in one of the abovementioned inert suspension media.

If the polymerization is carried out as a suspension or solution polymerization, an inert solvent customary for the Ziegler low-pressure process is used. For example, the polymerization is carried out in an aliphatic or cycloaliphatic hydrocarbon, for example propane, butane, hexane, heptane, isooctane, cyclohexane or methylcyclohexane. It is also possible to use a petroleum or hydrogenated diesel oil fraction, toluene can also be used. Preference is given to carrying out the polymerization in the liquid monomer.

Before addition of the catalyst, in particular the supported catalyst system (comprising the metallocene of the invention and a supported cocatalyst), it is possible to additionally add an aluminum alkyl compound such as trimethylaluminum, triethylaluminum, triisobutylaluminum, trioctylaluminum or isoprenylaluminum to the reactor for making the polymerization system inert (for example for removing catalyst poisons present in the olefin). This is added to the polymerization system in a concentration of from 100 to 0.01 mmol of Al per kg of reactor contents. Preference is given to triisobutylaluminum and triethylaluminum in a concentration of from 10 to 0.1 mmol of Al per kg of reactor contents. This enables a low molar Al/$M^1$ ratio to be selected in the synthesis of a supported catalyst system.

If inert solvents are used, the monomers are metered in in gaseous or liquid form.

The polymerization time can be any desired, since the catalyst system to be used in the process of the invention displays only a small time-dependent drop in the polymerization activity.

The specific metallocene compounds described in the present invention is suitable for preparing polyolefins.

The use of hydrogen or increasing the polymerization temperature makes it possible to obtain polyolefins of low molecular weight, for example waxes, whose hardness or melting point can be varied by means of the comonomer content.

Alternatively, selection of the polymerization conditions also makes it possible to prepare high molecular weight polyolefins which are suitable as thermoplastic materials. These are particularly suitable for producing shaped bodies such as films, plates or large hollow bodies (e.g. pipes).

Selection of the polymerization process and the type(s) of comonomer and also amount(s) of comonomer(s) enables olefin copolymers, e.g. ethylene-propylene-1,4-hexadiene terpolymers, to be prepared.

EXAMPLES

Example 1

Bis(dimethylamido)[$\eta^5$:$\eta^5$-2,2-(cyclopentadienyl)(indenyl)propylidene]-zirconium 416 mg (1.55 mmol) of Zr(NMe$_2$)$_4$ are dissolved in 25 ml of toluene and admixed at −78° C. with 345 mg (1.55 mmol) of 2-cyclopentadienyl-2-indenylpropane. The mixture subsequently warms up to room temperature while stirring. After 12 hours, it is heated at 80° C. for 3 hours. Volatile materials are removed in an oil pump vacuum. 613 mg (1.53 mmol, 99%) of bis(dimethylamido)[$\eta^5$:$\eta^5$-2,2-(cyclopentadienyl)(indenyl)propylidene]-zirconium remain as an orange solid.

Analysis:

$^1$H-NMR (400 MHz, C$_6$D$_6$, 25° C.): [ppm]δ=1.57, 1.89 (s, 6H; C(CH$_3$)$_2$), 2.46, 2.81 (s, 12H; N(CH$_3$)$_2$), 5.29 (q, 1H, $^3$J(H,H)=2.4 Hz; olefin. CH in C$_5$H$_4$), 5.80 (m, 2H; olefin. CH in C$_5$H$_4$ und C$_9$H$_7$), 5.99 (q, 1H. $^3$J(H,H)=2.4 Hz; olefin. CH in C$_5$H$_4$), 6.08 (q, 1H, $^3$J(H,H)=1.8 Hz; olefin. CH in C$_5$H$_4$), 6.59 (d, 1H, $^3$J(H,H)=3.0 Hz; olefin. CH in C$_9$H$_7$), 6.69 (dd, 1H, $^3$J(H,H)=6.7 Hz; olefin. CH in C$_9$H$_7$), 6.87 (dd, 1H, $^3$J(H,H)=6.7 Hz; olefin CH in C$_9$H$_7$), 7.49 (d, 1H, $^3$J(H,H)=7.9 Hz; olefin CH in C$_9$H$_7$), 7.62 (d, 1H, $^3$J(H,H)=7.9 Hz; olefin CH in C$_9$H$_7$).

$^{13}$C{$^1$H}-NMR (100.5 MHz, C$_6$D$_6$, 25° C.): [ppm]δ=26.2, 26.7 (s; C(CH$_3$)$_2$), 38.1 (s; C(CH$_3$)$_2$), 47.2, 48.3 (s; N(CH$_3$)$_2$), 102.2, 102.2, 102.8, 107.8, 109.6 (s; olefin. CH), 111.8 (s; olefin C), 114.3 (s; olefin. CH), 118.2 (s; olefin C), 122.7, 123.2, 123.6, 125.7 (s; aromat. CH).

$^{13}$C-NMR (100.5 MHz, C$_6$D$_6$ 25° C.): [ppm]δ=26.2, 26.7 (q, $^1$J(C,H)=132.0 Hz; C(CH$_3$)$_2$), 38.1 (s; C(CH$_3$)$_2$), 47.2 (q, $^1$J(C,H)=125.9 Hz; N(CH$_3$)$_2$), 48.3 (q, $^1$J(C,H) =125.8 Hz; N(CH$_3$)$_2$), 102.0 (d, $^1$J(C,H)=167.3 Hz; olefin. CH), 102.2 (d, $^1$J(C,H)=176.0 Hz; olefin. CH), 102.8 (d, $^1$J(C,H)=172.5 Hz; olefin. CH), 107.8 (d, $^1$J(C,H)=170.0 Hz; olefin. CH), 109.6 (d, $^1$J(C,H)=164.1 Hz; olefin. CH), 111.8 (s; olefin. C), 114.3 (d, $^1$J(C,H)=170.9 Hz; olefin. CH), 118.2 (s; olefin. C), 122.7 (d, $^1$J(C,H)=166.0 Hz; aromat. CH), 123.2 (d, $^1$J(C,H)=160.0; aromat. CH), 123.6 (d, $^1$J(C,H)=159.1 Hz; aromat. CH), 125.7 (d, $^1$J(C,H)=162.0 Hz; aromat. CH).

MS (CI): m/e (%)=708 (10) [2M$^+$—2NMe$_2$], 398 (100) [M$^+$], 355 (45) [M$^+$—NMe$_2$], 311 (21) [M$^+$—2NMe$_e$].

Example 2

Bis(dimethylamido)[$\eta^5$:$\eta^5$-2,2-(cyclopentadienyl)(indenyl)propylidine]-hafnium 833 mg (2.35 mmol) of Hf(NME$_2$)$_4$ are dissolved in 30 ml of p-xylene and admixed at −78° C. with 522 mg (2.35 mmol) of 2-cyclopentadienyl-2-indenylpropane. The mixture subsequently warms up to room temperature while stirring. After 2 hours, it is heated at 80° C. for 8 hours. Volatile materials are removed in an oil pump vacuum. The orange solid thus obtained is recrystallized from a little pentane. This gives 1.19 g (2.23 mmol, 95%), of bis(dimethylamido)[$\eta^5$:$\eta^5$-2,2-(cyclopentadienyl)(indenyl)propylidine]-hafnium as an orange solid.

Analysis:

$^1$H-NMR (400 MHz, C$_6$D$_6$, 25° C.): [ppm]δ=1.57, 1.88 (s, 6H; C(CH$_3$)$_2$), 2.51, 2.85 (s, 12H; N(CH$_3$)$_2$), 5.29 ("q", 1H; olefin. CH in C$_5$H$_4$), 5.70–5.80 (m, 2H; olefin. CH in C$_5$H$_4$ and C$_9$H$_7$), 6.00 (m, 1H; olefin CH in C$_5$H$_4$), 6.04 (m, 1H; olefin CH in C$_5$H$_4$), 6.53 (d, 1H; $^3$J(H,H)=3.0 Hz; olefin. CH in C$_9$H$_7$), 6.71 (t, 1H, $^3$J(H,H)=6.7 Hz; olefin CH in C$_9$H$_7$), 6.87 (t, 1H, $^3$J(H,H)=7.0 Hz; olefin. CH in C$_9$H$_7$), 7.49 (d, 1H, $^3$J(H,H)=7.9 Hz; olefin. CH in C$_9$H$_7$), 7.63 (d, 1H, $^3$J(H,H)=8.6 Hz; olefin. CH in C$_9$H$_7$).

$^{13}$C{$^1$H}-NMR (100.5 MHz, C$_6$D$_6$, 25° C.): [ppm]δ= 26.3, 26.8 (s; C(CH$_3$)$_2$), 38.2 (s; C(CH$_3$)$_2$), 47.2 (s; N(CH$_3$)$_2$), 100.6, 101.1, 101.8, 107.2, 108.6 (s; olefin. CH), 111.7 (s; olefin C), 113.6 (s; olefin. CH), 117.9 (s; olefin C), 122.7, 123.3, 123.9, 125.7 (s; aromat. CH).

MS (cI): me/ (%)=620 (100), 600 (18), 512 (24), 497 (28), 442 (17), 399 (25), 222 (26), 207 (26), 115 (8), 107 (20).

We claim:

1. A metallocene compound of the formula I:

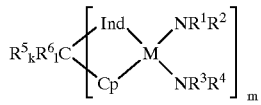

(I)

where

Cp is an unsubstituted or substituted cyclopentadienyl group,

Ind is an unsubstituted or substituted indenyl group, wherein the substituted indenyl group is substituted with a hydrocarbon which can optionally contain a heteroatom, M is a tetravalent metal, $R^1$, $R^2$, $R^3$ and $R^4$ are, independently of one another, identical or different and are each a hydrogen atom or a $C_1$–$C_{20}$-hydrocarbon radical, $R^5$ and $R^6$ are, independently of one another, identical or different and are each a hydrogen atom or a $C_1$–$C_{30}$-hydrocarbon radical, m is 1 or 2, k and l are each 1 when m is 1, and k and l are each zero when m is 2, with the proviso that Cp is not identical to Ind, and if a substituted or unsubstituted fluorenyl group is present, it must fall under the substituted Cp designation, and not under the substituted Ind designation.

2. A catalyst comprising the combination comprising at least one metallocene compound of the formula I as claimed in claim 1 and at least one cocatalyst.

3. A catalyst as claimed in claim 2, wherein the cocatalyst of said combination is an aluminum compound, a boron compound or both an aluminum compound and a boron compound.

4. A catalyst as claimed in claim 2, further comprising a support.

5. A catalyst as claimed in claim 2, wherein the metallocene compound of the formula I is prepolymerized.

6. A process for preparing a polyolefin by polymerizing at least one olefin in the presence of a catalyst as claimed in claim 2.

7. A polyolefin prepared by the process as claimed in claim 6.

8. A shaped part comprising a polyolefin as claimed in claim 7.

9. A process for preparing a polyolefin by polymerizing at least one olefin in the presence of a catalyst comprising a metallocene of the formula I as claimed in claim 1 or a cationic and or labile coordination form thereof.

10. A process for preparing a metallocene compound of the formula I as claimed in claim 1 by reacting a compound of the formula II, where Cp is an unsubstituted or substituted cyclopentadienyl group, Ind is unsubstituted or substituted indenyl, $R^5$ and $R^6$ are, independently of one another, identical or different and are each a hydrogen atom or a $C_1$–$C_{20}$-hydrocarbon radical, m is 1 or 2 and k and l are 1 when m is 1 and k and l are zero when m is 2, with a compound of the formula III, where M is a tetravalent metal and $R^1$, $R^2$, $R^3$ and $R^4$ are, independently of one another, identical or different and are each a hydrogen atom or a $C_1$–$C_{20}$-hydrocarbon radical

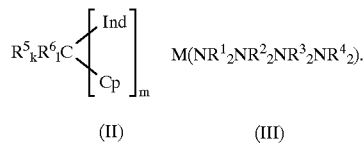

(II)        (III)

11. A metallocene compound of the formula I as claimed in claim 1, wherein $R^5$ and $R^6$, are the same or different and are each methyl, ethyl, butyl or phenyl; $R^1$, $R^2$, $R^3$ and $R^4$ are the same or different and are each $C_1$–$C_{20}$-alkyl or $C_6$–$C_{14}$-aryl; and M is titanium, zirconium or hafnium.

12. A catalyst as claimed in claim 2, wherein said cocatalyst has converted said metallocene to a cation and has stabilized the metallocene by labile coordination.

13. A catalyst as claimed in claim 12, wherein said cocatalyst is:

an aluminoxane, an aluminum alkyl compound, a boron compound of the formula

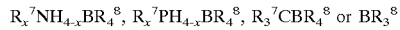

where x is from 1 to 4, the $R^7$ radicals are identical or different and are $C_1$–$C_{10}$-alkyl or $C_6$–$C_{18}$-aryl, or two $R^7$ radicals together with the atoms connecting them form a ring, and the $R^8$ radicals are identical or different and are $C_6$–$C_{18}$ aryl, optionally substituted by alkyl, haloalkyl, or fluorine, or a combination thereof.

14. The metallocene compound of the formula I as claimed in claim 1, wherein Ind is the unsubstituted indenyl group or the substituted indenyl group which is substituted with an alkyl group.

15. The metallocene compound of formula I as claimed in claim 1, wherein Cp is the unsubstituted cyclopentadienyl group or the substituted cyclopentadienyl group which is substituted with an alkyl group.

16. The metallocene compound of the formula I as claimed in claim 1, wherein the heteroatom is silicon.

17. A metallocene compound which is:

bis(dimethylamido)[$\eta^5$:$\eta^5$-2,2-(cyclopentadienyl)(indenyl)propylidene)]-zirconium, bis(dimethylamido)[$\eta^5$:$\eta^5$-2,2-(cyclopentadienyl)(indenyl)propylidene)]-hafnium, bis(dimethylamido)[$\eta^5$:$\eta^5$-2,2-(fluorenyl)(indenyl)propylidene)]zirconium, bis(dimethylamido)[$\eta^5$:$\eta^5$-2,2-(fluorenyl)(indenyl)propylidene)]hafnium, bis(dimethylamido)[$\eta^5$:$\eta^5$-2,2-(methylcyclopentadienyl)(indenyl)propylidene)]zirconium, bis(dimethylamido)[$\eta^5$:$\eta^5$-2,2-(fluorenyl)(2-methylindenyl)propylidene)]-zirconium, bis(dimethylamido)[$\eta^5$:$\eta^5$-2,2-(tetramethylcyclopentadienyl)(indenyl)propylidene)]zirconium, bis(dimethylamido)[$\eta^5$:$\eta^5$-2,2-(fluorenyl)(2-ethylindenyl)propylidene)]-zirconium, bis(dimethylamido)[$\eta^5$:$\eta^5$-2,2-(cyclopentadienyl)(2-methylindenyl)propylidene)]zirconium, bis(dimethylamido)[$\eta^5$:$\eta^5$-2,2-(cyclopentadienyl)(2-ethylindenyl)propylidene)]-zirconium, bis(dimethylamido)[η⁵:η⁵-2,2-(cyclopentadienyl)(3-trimethylsilylindenyl)propylidene)]zirconium,
bis(dimethylamido)[η⁵:η⁵-2,2-(methylcyclopentadienyl)(2-methylindenyl)propylidene)]zirconium,
bis(dimethylamido)[η⁵:η⁵-2,2-(methylcyclopentadienyl)(2-ethylindenyl)propylidene)]zirconium,
bis(dimethylamido)[η⁵:η⁵-2,2-(methylcyclopentadienyl)(3-trimethylsilylindenyl)propylidene)]zirconium,
bis(diethylamido)[η⁵:η⁵-2,2-(cyclopentadienyl)(indenyl)propylidene)]-zirconium,
bis(diethylamido)[η⁵:η⁵-2,2-(cyclopentadienyl)(indenyl)propylidene)]-hafnium,
bis(diethylamido)[η⁵:η⁵-2,2-(fluorenyl)(indenyl)propylidene)]zirconium,
bis(diethylamido)[η⁵:η⁵-2,2-(fluorenyl)(indenyl)propylidene)]hafnium,
bis(diethylamido)[η⁵:η⁵-2,2-(methylcyclopentadienyl)(indenyl)propylidene)]zirconium,
bis(diethylamido)[η⁵:η⁵-2,2-(fluorenyl)(2-methylindenyl)propylidene)]-zirconium,
bis(diethylamido)[η⁵:η⁵-2,2-(tetramethylcyclopentadienyl)(indenyl)propylidene)]zirconium,
bis(diethylamido)[η⁵:η⁵-2,2-(fluorenyl)(2-ethylindenyl)propylidene)]-zirconium,
bis(diethylamido)[η⁵:η⁵-2,2-(cyclopentadienyl)(2-methylindenyl)propylidene)]zirconium,
bis(diethylamido)[η⁵:η⁵-2,2-(cyclopentadienyl)(2-ethylindenyl)propylidene)]-zirconium,
bis(diethylamido)[η⁵:η⁵-2,2-(cyclopentadienyl)(3-trimethylsilylindenyl)propylidene)]zirconium,
bis(diethylamido)[η⁵:η⁵-2,2-(methylcyclopentadienyl)(2-methylindenyl)propylidene)]zirconium,
bis(diethylamido)[η⁵:η⁵-2,2-(methylcyclopentadienyl)(2-ethylindenyl)propylidene)]zirconium,
bis(diethylamido)[η⁵:η⁵-2,2-(methylcyclopentadienyl)(3-trimethylsilylindenyl)propylidene)]zirconium,
bis(methylethylamido)[η⁵:η⁵-2,2-(cyclopentadienyl)(indenyl)propylidene)]-zirconium,
bis(methylethylamido)[η⁵:η⁵-2,2-(cyclopentadienyl)(indenyl)propylidene)]-hafnium,
bis(methylethylamido)[η⁵:η⁵-2,2-(fluorenyl)(indenyl)propylidene)]zirconium,
bis(methylethylamido)[η⁵:η⁵-2,2-(fluorenyl)(indenyl)propylidene)]hafnium,
bis(methylethylamido)[η⁵:η⁵-2,2-(methylcyclopentadienyl)(indenyl)propylidene)]zirconium,
bis(methylethylamido)[η⁵:η⁵-2,2-(fluorenyl)(2-methylindenyl)propylidene)]-zirconium,
bis(methylethylamido)[η⁵:η⁵-2,2-(tetramethylcyclopentadienyl)(indenyl)propylidene)]zirconium,
bis(methylethylamido)[η⁵:η⁵-2,2-(fluorenyl)(2-ethylindenyl)propylidene)]-zirconium,
bis(methylethylamido)[η⁵:η⁵-2,2-(cyclopentadienyl)(2-methylindenyl)propylidene)]zirconium,
bis(methylethylamido)[η⁵:η⁵-2,2-(cyclopentadienyl)(2-ethylindenyl)propylidene)]-zirconium,
bis(methylethylamido)[η⁵:η⁵-2,2-(cyclopentadienyl)(3-trimethylsilylindenyl)propylidene)]zirconium,
bis(methylethylamido)[η⁵:η⁵-2,2-(methylcyclopentadienyl)(2-methylindenyl)propylidene)]zirconium,
bis(methylethylamido)[η⁵:η⁵-2,2-(methylcyclopentadienyl)(2-ethylindenyl)propylidene)]zirconium,
bis(methylethylamido)[η⁵:η⁵-2,2-(methylcyclopentadienyl)(3-trimethylsilylindenyl)propylidene)]zirconium,
bis(pyrrolidinoamido)[η⁵:η⁵-2,2-(cyclopentadienyl)(indenyl)propylidene)]-zirconium,
bis(pyrrolidinoamido)[η⁵:η⁵-2,2-(cyclopentadienyl)(indenyl)propylidene)]-hafnium,
bis(pyrrolidinoamido)[η⁵:η⁵-2,2-(fluorenyl)(indenyl)propylidene)]zirconium,
bis(pyrrolidinoamido)[η⁵:η⁵-2,2-(fluorenyl)(indenyl)propylidene)]hafnium,
bis(pyrrolidinoamido)[η⁵:η⁵-2,2-(methylcyclopentadienyl)(indenyl)propylidene)]zirconium,
bis(pyrrolidinoamido)[η⁵:η⁵-2,2-(fluorenyl)(2-methylindenyl)propylidene)]-zirconium,
bis(pyrrolidinoamido)[η⁵:η⁵-2,2-(tetramethylcyclopentadienyl)(indenyl)propylidene)]zirconium,
bis(pyrrolidinoamido)[η⁵:η⁵-2,2-(fluorenyl)(2-ethylindenyl)propylidene)]-zirconium,
bis(pyrrolidinoamido)[η⁵:η⁵-2,2-(cyclopentadienyl)(2-methylindenyl)propylidene)]zirconium,
bis(pyrrolidinoamido)[η⁵:η⁵-2,2-(cyclopentadienyl)(2-ethylindenyl)propylidene)]-zirconium,
bis(pyrrolidinoamido)[η⁵:η⁵-2,2-(cyclopentadienyl)(3-trimethylsilylindenyl)propylidene)]zirconium,
bis(pyrrolidinoamido)[η⁵:η⁵-2,2-(methylcyclopentadienyl)(2-methylindenyl)propylidene)]zirconium,
bis(pyrrolidinoamido)[η⁵:η⁵-2,2-(methylcyclopentadienyl)(2-ethylindenyl)propylidene)]zirconium,
bis(pyrrolidinoamido)[η⁵:η⁵-2,2-(methylcyclopentadienyl)(3-trimethylsilylindenyl)propylidene)]zirconium.

18. A metallocene compound of the formula I:

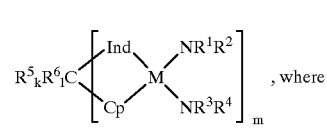, where (I)

where

Cp is an unsubstituted or substituted cyclopentadienyl group,

Ind is an unsubstituted or substituted indenyl group, wherein the substituted indenyl group is substituted with a hydrocarbon containing a heteroatom, M is a tetravalent metal, $R^1$, $R^2$, $R^3$ and $R^4$ are, independently of one another, identical or different and are each a hydrogen atom or a $C_1$–$C_{20}$-hydrocarbon radical, $R^5$ and $R^6$ are, independently of one another, identical or different and are each a hydrogen atom or a $C_1$–$C_{30}$-hydrocarbon radical, m is 1 or 2, k and l are each 1 when m is 1, and k and l are each zero when m is 2,
with the proviso that Cp is not identical to Ind, and if a substituted or unsubstituted fluorenyl group is present, it must fall under the substituted Cp designation, and not under the substituted Ind designation.

19. The metallocene compound of formula I as claimed in claim 1, wherein the substituted indenyl group is 4,5-benzoindenyl, 2-methyl-4,5-benzoindenyl or 2-methyl-α-acenaphthindenyl.

* * * * *

UNITED STATES PATENT AND TRADEMARK OFFICE
CERTIFICATE OF CORRECTION

PATENT NO. : 6,040,469
DATED : March 21, 2000
INVENTOR(S) : Michael Riedel, et al.

It is certified that error appears in the above-identified patent and that said Letters Patent is hereby corrected as shown below:

In claim 9, line 4, (column 9, line 56), delete -- or --.

In claim 17, fourth line from the end of the claim, (column 12, line 39), after the comma "," add -- or -- .

Signed and Sealed this

Nineteenth Day of December, 2000

Attest:

Q. TODD DICKINSON

Attesting Officer

Commissioner of Patents and Trademarks